United States Patent [19]

Ohtani et al.

[11] Patent Number: 5,710,253

[45] Date of Patent: *Jan. 20, 1998

[54] METHOD FOR DECOLORING HUMAN SERUM ALBUMIN

[75] Inventors: Wataru Ohtani; Naoto Furuhata; Akinori Sumi; Munehiro Noda; Takao Ohmura, all of Osaka, Japan

[73] Assignee: The Green Cross Corporation, Osaka, Japan

[*] Notice: The term of this patent shall not extend beyond the expiration date of Pat. No. 5,440,018.

[21] Appl. No.: 358,302

[22] Filed: Dec. 19, 1994

[30] Foreign Application Priority Data

Dec. 17, 1993 [JP] Japan ................................. 5-318710
Dec. 17, 1993 [JP] Japan ................................. 5-318724

[51] Int. Cl.⁶ ..................... C07K 1/36; C07K 14/765; C07K 1/16; A61K 38/38
[52] U.S. Cl. ..................... 530/364; 530/402; 530/408; 530/416; 530/427; 514/12
[58] Field of Search ................... 530/363, 364, 530/416, 402, 408, 427, 829; 514/12, 21

[56] References Cited

U.S. PATENT DOCUMENTS

| | | | |
|---|---|---|---|
| 4,016,149 | 4/1977 | Travis et al. | 530/364 |
| 4,093,612 | 6/1978 | Travis et al. | 530/364 |
| 4,156,681 | 5/1979 | Schneider et al. | 530/364 |
| 5,187,261 | 2/1993 | Latta et al. | 530/363 |
| 5,294,699 | 3/1994 | Ohmura et al. | 530/364 |
| 5,369,020 | 11/1994 | Sumi et al. | 435/69.6 |
| 5,440,018 | 8/1995 | Ohmura et al. | 530/363 |

*Primary Examiner*—Nancy Degen
*Attorney, Agent, or Firm*—Sughrue, Mion, Zinn, Macpeak & Seas PLLC

[57] ABSTRACT

A method for decoloring a recombinant human serum albumin by treating the albumin with a reducing agent is disclosed. Also, a method for decoloring a recombinant human serum albumin by treating the albumin with a method removing free polysaccharides with a cation exchanger followed by heat treatment is disclosed. The present invention provides a recombinant human serum albumin, coloring of which is fully suppressed by preventing binding of certain coloring components, which are contained in the raw materials or contaminants secreted by a microorganism, to human serum albumin so as not to cause coloring of the human serum albumin.

15 Claims, No Drawings

METHOD FOR DECOLORING HUMAN SERUM ALBUMIN

FIELD OF THE INVENTION

This invention relates to a method for decoloring recombinant human serum albumin obtained by gene manipulation techniques.

BACKGROUND OF THE INVENTION

Albumin, especially human serum albumin (HSA), is an important protein of the circulatory system. The protein is produced in the liver and has a major role in maintaining normal osmotic pressure of body fluids, such as blood. It also serves as a carrier of various molecules.

HSA is administered under various clinical conditions. For example, in the case of shock or burn injury, it is necessary, in general, to administer HSA frequently to restore blood volume and to alleviate other injury-related symptoms. Patients suffering from hypoproteinemia and fetal erythroblastosis sometimes require HSA treatment. In other words, a common indication for HSA administration is a loss of body fluids, such as during a surgical procedure, shock, burn injury or hypoproteinemia which causes edema.

Currently, HSA is produced mainly as a fractionated product of collected blood. Such a production process, however, has disadvantages in that it is not economical and the supply of blood is sporadic. In addition, collected blood sometimes contains undesirable substances, such as hepatitis virus. In consequence, it is profitable to develop a material which can be used as a substitute for HSA obtained from collected blood.

Recent advances in recombinant DNA techniques have rendered possible microbial production of various types of useful polypeptides, and, as a result, a number of mammalian polypeptides have been produced in various microorganisms. With regard to HSA, establishing techniques for the large scale production of HSA by recombinant methods and subsequent high grade purification is in progress.

However, in the case of producing HSA by means of gene manipulation techniques, it is highly probable that an HSA preparation of interest will be contaminated by certain coloring components, which are contained in the raw materials or secreted by a microorganism during culturing of the host microorganism or are introduced during purification of the resulting HSA, and that these contaminants bind to HSA to cause coloring of the HSA itself. What is more, such contaminants cannot be removed sufficiently by means of any prior art process for the purification of plasma-derived HSA.

SUMMARY OF THE INVENTION

An object of the instant invention is to provide human serum albumin obtained by means of gene manipulation techniques, coloring of which can be sufficiently suppressed by removing the above-described coloring components and contaminants that have not been fully removed by means of any prior art process-for the purification of plasma-derived HSA.

Under the above-described circumstances, the instant inventors have conducted intensive studies and, as a result, found that HSA obtained by gene manipulation techniques can be decolored by treating the HSA with a reducing agent or subjecting the HSA to heat treatment during the purification procedure of the HSA.

Thus, the present invention relates to a method for decoloring recombinant human serum albumin, which comprises treating the HSA with a reducing agent during the purification procedure.

The present invention also relates to a method for decoloring recombinant human serum albumin, which comprises subjecting the HSA to heat treatment under the conditions that free polysaccharides have been removed. More specifically, the recombinant HSA is heat treated after treating the HSA with a cation exchanger treatment during the purification procedure.

DETAILED DESCRIPTION OF THE INVENTION

The starting recombinant HSA used in the instant invention can be produced by cultivating HSA-producing host cells, such as *Escherichia coli*, various yeast species, *Bacillus subtilis*, Aspergillus and animal cells, to effect extracellular expression (secretory expression) of the HSA.

The recombinant HSA to be treated for decoloration according to the instant invention can be isolated and purified as described below.

(1) Preparation and Culturing of HSA Producing Host Cells and Isolation and Recovery of HSA The origin of the starting recombinant HSA used in the instant invention is not limited, provided the HSA is prepared by gene manipulation techniques. The HSA-producing host to be used in the instant invention is not limited, provided it is prepared by gene manipulation techniques. Hence the host can be selected from hosts already reported in publications, as well as those hosts that will be developed in the future. Illustrative examples of the host include microbial cells, such as *Escherichia coli*, various yeast species, *Bacillus subtilis*, and animal cells, which have been made into HSA producers. Particularly preferred hosts are yeast species, especially those belonging to the genus Saccharomyces, such as *Saccharomyces cerevisiae*, the genus Pichia, such as *Pichia pastoris* or the genus Kluyveromyces, such as *Kluyveromyces lactis*. Also, auxotrophic strains or antibiotic-sensitive strains may be used. Preferably, *Saccharomyces cerevisiae* AH22 (a, his 4, leu 2, can 1), *Pichia pastoris* GTS115 (his 4) and *Kluyveromyces lactis* MW-98-8C ($\alpha$, uraA, arg, lysK$^+$, pKD1$^\circ$) are used. Preferably, the HSA used in the instant invention is produced using these hosts.

Preparation of the HSA-producing hosts, production of HSA by culturing the hosts, and isolation and recovery of HSA from the resulting culture broth may be effected using known techniques or modified procedures thereof.

For example, preparation of an HSA-producing host (or an HSA-producing strain) may be effected using a process in which a natural human serum albumin gene is used (JP-A-58-56684 corresponding to EP-A-73646, JP-A-58-90515 corresponding to EP-A-79739 and JP-A-58-150517 corresponding to EP-A-91527), a process in which a modified human serum albumin gene is used (JP-A-62-29985 and JP-A-1-98486 corresponding to EP-A-206733), a process in which a synthetic signal sequence is used (JP-A-1-240191 corresponding to EP-A-329127), a process in which a serum albumin signal sequence is used (JP-A-2-167095 corresponding to EP-A-319641), a process in which a recombinant plasmid is introduced into a chromosome (JP-A-3-72889 corresponding to EP-A-399455), a process in which hosts are fused (JP-A-3-53877 corresponding to EP-A-409156), a process in which a mutation is generated in a methanol containing medium, a process in which a mutant AOX$_2$ promoter is used (EP-A-506040), a process in which HSA is expressed in *B. subtilis* (JP-A-62-215393 corresponding to EP-A-229712), a process in which HSA is expressed in yeast (JP-A-60-41487 corresponding to EP-A-123544, JP-A-63-39576 corresponding to EP-A-248657 and JP-A-63-74493 corresponding to EP-A-251744) and a process in which HSA is expressed in Pichia (JP-A-2-104290 corresponding to EP-A-344459) (the term "JP-A" used herein means a Japanese published unexamined patent application).

Culturing of an HSA-producing host (an HSA production process) may be, carried out using known processes disclosed in the above-mentioned references; or in accordance with a process disclosed in JP-A-3-83595, in which high concentration substrate inhibition of HSA producer cells is avoided by gradually adding a high concentration glucose solution to the medium by means of batch feed fermentation, thereby enabling production of both the producer cells and the product in high concentrations; or in accordance with another process disclosed in JP-A-4-293495 corresponding to EP-A-504823, in which productivity of HSA is improved by adding fatty acids to the medium.

Isolation and recovery of HSA may be carried out using known processes disclosed in the above-mentioned references, or in accordance with a process disclosed in JP-A-3-103188 corresponding to EP-A-420007, in which proteases are inactivated by heat treatment; or a coloration inhibition process disclosed in JP-A-4-54198 corresponding to U.S. Pat. No. 5,132,404 or EP-A-464590, in which HSA is separated from coloring substances using at least one adsorbent selected from the group consisting of anion exchangers, hydrophobic carriers and activated charcoal.

(2) Initial Purification of HSA

The HSA can be initially purified by known methods, such as fractionation, adsorption chromatography, gel filtration, density-gradient centrifugation or dialysis.

A suitable initial purification method contains the following steps:

(i) passing a culture supernatant of a host that expresses HSA, through a first ultrafiltration membrane having a molecular weight exclusion limit of from 100,000 to 500,000 and then through a second ultrafiltration membrane having a molecular weight exclusion limit of from 1,000 to 50,000 to yield a first filtrate;

(ii) heat-treating the first filtrate at 50° to 70° C. for 30 minutes to 5 hours to yield a heated sample;

(iii) acid-treating the heated sample at a pH of from 3 to 5 to yield an acid-treated sample;

(iv) passing the acid-treated sample through ultrafiltration membrane having a molecular weight exclusion limit of from 100,000 to 500,000 to yield a second filtrate;

(v) exposing the second filtrate to a cation exchanger, at a pH of 3 to 5 and a salt concentration of 0.01 to 0.2M, and then exposing said cation exchanger to a pH of 8 to 10 and a salt concentration of 0.2 to 0.5M to yield a first eluate;

(vi) allowing the first eluate to contact a carrier for hydrophobic chromatography at a pH of 6 to 8 and a salt concentration of 0.01 to 0.5M, and recovering non-adsorbed fractions to yield a second eluate; and (vii) allowing the second eluate to contact an anion exchanger at a pH of 6 to 8 and a salt concentration of 0.01 to 0.1M, and recovering non-adsorbed fractions to yield said albumin.

Alternatively, instead of the aforementioned step (vi), an alternative step may be employed in which the corresponding sample is allowed to contact with a hydrophobic chromatography carrier at pH 6 to 8 with a salt concentration of 1 to 3M and subsequently eluted at pH 6 to 8 with a salt concentration of 0.01 to 0.5M; instead of the aforementioned step (vii), an alternative step may be employed in which the corresponding sample is allowed to contact with an anion exchanger at pH 6 to 8 with a salt concentration of 0.01 to 0.05M and subsequently eluted at pH 6 to 8 with a salt concentration of 0.05 to 1M; or an additional step in which salting out is effected at pH 3 to 5 with a salt concentration of 0.5 to 3M and the precipitated fraction is recovered may be introduced between the aforementioned steps (v) and (vi), or (vi) and (vii), or after (vii).

(3) High Grade Purification

The following treatments may be carried out in order to purify HSA to a high degree.

(i) Chelate Resin Treatment

The chelate resin treatment is intended for decoloration of the HSA. This treatment can be part of the above purification procedure, preferably as a final step, which is carried by allowing HSA to contact with a chelate resin that has a specified ligand moiety. Preferably, the carrier moiety of the chelate resin will have a hydrophobic nature. Examples of such a type of carrier moiety include a copolymer of styrene and divinylbenzene, and a copolymer of acrylic acid and methacrylic acid.

Examples of the ligand moiety include a thiourea group, as well as a polyamine group (including a polyalkylene polyamine group, such as polyethylene polyamine) which contains, in one molecule, a plurality of sub-groups consisting of a polyol group, such as an N-methylglucamine group, an imino group, an amino group, and an ethyleneimino group. Illustrative examples of preferred commercially available chelate resins having the above-described carrier and ligand moieties include DIAION CRB02 (ligand moiety, N-methylglucamine group, available from Mitsubishi Kasei Corp.), DIAION CR20 (ligand moiety, —NH$(CH_2CH_2NH)_n$H, available from Mitsubishi Kasei Corp.), LEWATIT TP214 (ligand moiety, —NHCSNH$_2$, available from Bayer) and AMBERLITE CG4000, all of which have a copolymer of styrene and divinylbenzene as the carrier moiety.

Preferred conditions for the chelate resin treatment are as follows.

pH: acidic or about neutral (pH 3 to 9, preferably 4 to 7),
period: at least 1 hour, preferably 6 hours or more,
ionic strength: 50 mmho or less, preferably 1 to 10 mmho,
mixing ratio: 0.1 to 100 g, preferably 1 to 10 g, of the resin based on 250 mg of HSA (wet basis).

(ii) Hydrophobic Chromatography

Free nonantigenic contaminants detectable by the phenol-sulfuric acid method are not fully removed from the HSA obtained through the above-described purification steps (i) to (vii) and the chelate resin treatment.

The HSA obtained through the above-described treatments is allowed to contact a carrier for hydrophobic chromatography at a pH of 2 to 5, preferably 3 to 4 and a salt concentration of 0.4 to 1M, preferably 0.4 to 0.7M. The elution can be effected at a pH of 6 to 8, preferably 6.5 to 7 and a salt concentration of 0.01 to 0.3M, preferably 0.05 to 0.2M. The above-described step (vi) may be replaced with this hydrophobic chromatography step. Thus, HSA which does not contain free nonantigenic contaminants detectable by the phenol-sulfuric acid method can be recovered.

The term "phenol-sulfuric acid treatment" used herein means the colorimetric determination of carbohydrates which comprises adding a phenol solution to a sample carbohydrate solution, adding concentrated sulfuric acid thereto, shaking the mixture to allow a furfural derivative derived from the carbohydrate utilizing heat of dissolution to react with phenol, and colorimetrically determining the resulting colored reaction product. The free nonantigenic contaminants detectable by the phenol-sulfuric acid method include neutral carbohydrates, such as pentose and hexose, monocarbohydrate glycoside, such as oligosaccharides, complex carbohydrates and uronic acid, and methylated carbohydrate. These contaminants do not cause antigen-antibody reaction with antibodies against producer host-derived substances.

Carriers for use in hydrophobic chromatography include those containing an alkyl group (butyl group, octyl group, octyldecyl group and the like), each group having 4 to 18 carbon atoms, and those containing a phenyl group. Illustrative examples of the butyl group-containing carriers include butyl-agarose, butyl-polyvinyl (trade name, Butyl Toyopearl, available from Tosoh Corp.), those of the octyl group-containing and octyldecyl group-containing carriers include octyl-agarose and octyldecyl-agarose, respectively, and those of the phenyl group-containing carrier include phenyl-cellulose (trade name, Phenyl Cellulofine, available from Seikagaku Corp.).

(iii) Treatment with Boric Acid or a Salt Thereof

HSA can be treated with boric acid or a salt thereof to remove antigenic producer host-derived contaminants as well as free nonantigenic contaminants detectable by the phenol-sulfuric acid method.

Examples of the boric acid include orthoboric acid, metaboric acid, and tetraboric acid. The salts thereof include alkali metal salts such as sodium salt and potassium salt, and alkaline earth metal salts such as calcium salt. Calcium tetraborate is preferably used. Boric acid or a salt thereof is added to a final concentration of about 0.01 to 1M, preferably about 0.05 to 0.2M. This treatment can be carried out at a pH of about 8 to 11, preferably about 9 to 10 for about 1 to 10 hours. This treatment is preferably effected at a low electric conductivity, for example, 1 mS or less. The HSA concentration is preferably low, for example, 5% or less, more preferably about 0.1 to 3%.

After the treatment with boric acid or a salt thereof, the precipitate formed is removed by, for example, centrifugation or filtration and the supernatant is recovered, concentrated and desalted.

(iv) Ultrafiltration

The HSA recovered after the above purification steps is preferably subjected to ultrafiltration using an ultrafiltration membrane having a molecular weight exclusion limit of about 100,000. Pyrogen can be removed by this ultrafiltration treatment.

(4) Decoloration (i) Treatment with a Reducing Agent

The treatment with a reducing agent can be carried out either during the purification procedure of the above (2) or during the high grade purification procedure of the above (3). This treatment can be carried out together with or immediately after any one of the above-described purification steps.

The reducing agent to be used in this treatment is not particularly-limited as long as it is a substance having reducing activity. Illustrative examples thereof include a low molecular weight compound containing an SH group, such as cysteine, cysteamine, cystamine, aminopropanethiol, methionine, ethionine or glutathione, sulfurous acid, hyposulfurous acid, pyrosulfurous acid, phosphorous acid-sulfurous acid, phosphorous acid-pyrosulfurous acid, sulfurous acid-pyrophosphoric acid, ascorbic acid or a salt thereof. The salts include an alkali metal salt, such as sodium salt or potassium salt, and alkaline earth metal salt such as calcium salt.

The HSA concentration during the treatment ranges from 0.01 to 25 w/v %, preferably 0.1 to 5 w/v %. The reducing agent is used in an amount of approximately 1 to 100 mM in the case of cysteine and approximately 0.001 to 10% in the case of sulfurous acid. The treatment can be carried out at the temperature ranging from 10° to 100° C., preferably 20° to 80° C., for 10 minutes to 240 hours, preferably 30 minutes to 120 hours.

Amine compounds which are known to suppress coloration (JP-A-5-260980) can be used in combination with the reducing agent. Examples of the amine compounds include alkylamines, diamines, guanidines, benzamidines, basic amino acids and aminophenylacetic acid. The alkylamines preferably contain 1 to 6 carbon atoms. Examples thereof include methylamine, ethylamine, propylamine, isopropylamine and butylamine. Examples of diamines includes alkylenediamines, particularly those having 1 to 6 carbon atoms, such as methylenediamine, etylenediamine or propylenediamine, N,N-dialkylalkylenediamine, particularly those containing an alkyl moiety and an alkylene moiety each having 1 to 6 carbon atoms, such as N,N-dimethylethylenediamine or N,N-diethylethylenediamine. Examples of the guanidines include guanidine, aminoguanidine and phenylguanidine. Examples of the benzamidines include benzamidine and p-aminobenzamidine. The basic amino acids include lysine or arginine.

The amine compound is used in an amount of 0.01 to 10 w/v %, preferably 0.1 to 1 w/v %.

When the SH compound is used, the treatment can be carried out at pH 6 to 8, preferably pH 6.5 to 7.5, particularly with accompanied with heat treatment at 50° to 100° C. When the heat treatment is not performed combinedly, namely the treatment is carried out at 40° C. or lower, the pH value ranges from 3 to 6, preferably 4 to 5. When ascorbic acid is used, the pH value ranges from 3 to 6, preferably 4 to 5. The other reducing agents can be used at pH 6 to 10, preferably 8 to 9.

The decoloration treatment using the reducing agent according to the present invention makes it possible to decrease the degree of coloring of HSA by 10 to 70% as compared with the HSA immediately before the treatment.

(ii) Heat Treatment After Cation Exchanger Treatment

This heat treatment can be carried out either immediately after the cation exchanger treatment (v) during the purification procedure (2), during the subsequent purification procedure including high grade purification procedure, or at a final step, under the conditions that free polysaccharides have been removed by the cation exchanger treatment (v). Specifically, the content of the free polysaccharides is reduced to approximately 5 mg/ml or lower when the HSA concentration is 250 mg/ml.

The heat treatment can be carried out at 50° to 100° C., preferably 60° to 80° C., for 10 minutes to 10 hours, preferably 30 minutes to 5 hours. The HSA concentration during the treatment ranges from 0.01 to 25 w/v %, preferably 0.1 to 5 w/v %. For completely stabilizing the HSA, the heat treatment is preferably carried out in the presence of a known stabilizer, such as acetyltryptophan or a salt thereof (e.g. sodium salt), fatty acid having 6 to 20 carbon atoms or a salt thereof (e.g. sodium salt) (JP-A-3-103188).

The heat treatment is preferably carried out in the presence of the above-described reducing agent.

The above-described amine compounds can also be used during the heat treatment.

Immediately after the heat treatment according to the present invention, the degree of coloring of HSA is reduced by 30 to 70%, as compared with that immediately before the treatment.

(5) Pharmaceutical Preparation

The thus obtained rHSA (or a composition containing the same) can be made into a pharmaceutical preparation in accordance with known techniques such as ultrafiltration, sterile filtration, dispensing, and lyophilization. Also, in order to ensure stability during its production steps and preservation stability after its production, acetyl tryptophan or a salt thereof (sodium salt for example) and sodium caprylate may be blended as stabilizing agents as the occasion demands. These stabilizing agents may be used in an approximate amount of from 0.01 to 0.2M, preferably from 0.02 to 0.05M. The sodium content may be 3.7 mg/ml or less. These stabilizing agents may be added prior to the steps of ultrafiltration, sterile filtration, dispensing, and/or lyophilization.

The rHSA pharmaceutical preparation thus obtained by ultrafiltration and sterile filtration is aseptically packed in a container in an administration unit. The term "packed in a container in an administration unit" as used herein means that an administration unit of the rHSA pharmaceutical preparation, for example, a liquid preparation containing 25% of rHSA having an approximate pH value of 6.4 to 7.4 and an osmotic pressure ratio of about 1, is packed in containers in 20 to 50 ml (5 to 12.5 g rHSA) portions; or it means that a liquid preparation containing 5% of the rHSA is packed in containers in 100 to 250 ml (5 to 12.5 g rHSA) portions. Examples of the container for use in the packing the rHSA pharmaceutical preparation include a glass container, a polyethylene container, a dealkalinized soft glass container (JP-A-4-210646), each having a capacity of 10 to 250 ml.

The present invention provides recombinant HSA free from coloration caused by the binding of certain coloring components (which are contained in the raw materials or are contaminants secreted by a microorganism) to HSA.

The following examples are provided to further illustrate the present invention. It is to be understood, however, that the examples are for purpose of illustration only and are not intended as a definition of the limits of the present invention.

REFERENCE EXAMPLE 1

Culturing of a HSA Producing Host (1) Used Strain, *Pichia pastoris* GCP101

A 5' non-coding region of the HSA gene was removed from a plasmid pHSA113 described in JP-A-2-104290—corresponding to EP-A-344459 containing a transcription unit that is constructed so as to express HSA under the control of an $AOX_1$ promoter to prepare an HSA expression plasmid pPGP1. pPGP1 contains cDNA encoding the amino acid sequence of normal HSA (both of the amino acid sequence of normal HSA and the base sequence of the genomic DNA encoding normal HSA are described in J. Biol. Chem., 261, 6747–6757 (1986)). Then, in accordance with a process disclosed in JP-A-2-104290 corresponding to EP-A-344459, the HSA expression plasmid pPGP1 was digested with NotI and the resulting NotI-digested fragment was substituted for the $AOX_1$ gene region of a *Pichia pastoris* strain GTS115 (his4) (NRRL deposition number Y-15851) to prepare a transformant PC4130. The strain does not grow well in a medium containing methanol as the carbon source (Mut⁻ strain) because of the deletion of the $AOX_1$ gene.

The strain PC4130 was inoculated into 3 ml of YPD medium (1% yeast extract, 2% Bacto Peptone and 2% glucose). After 24 hours of culturing, the cells were inoculated into 50 ml of YPD medium so that the cell density could be adjusted to initial turbidity with an $OD_{540}$ of 0.1. After 3 days of culturing at 30° C., the resulting cells again were inoculated into 50 ml of YPD medium at an initial cell turbidity of 0.1 at $OD_{540}$. Thereafter, subculturing was repeated every 3 days in the same manner. After each subculturing, cells were diluted with sterile water and poured onto a 2% MeOH-YNBw/oa.a. plate (0.7% Yeast Nitrogen Base without Amino Acids, 2% methanol and 1.5% agar powder) in an inoculum size of $10^7$ cells/plate, followed by 5 days of culturing at 30° C. to judge the present/absence of colonies. Twenty colonies were found on the 2% MeOH-YNBw/oa.a. plate after 12 days of the successive subculturing. Mut⁻ strains can hardly grow on the 2% MeOH-YNBw/oa.a. medium while Mut⁺ strains can grow well. That is, the advent of a colony means that the strain acquired the capacity of increased methanol assimilation and thus a Mut⁺ strain was obtained. One of the thus obtained colonies was diluted appropriately with sterile water and spread onto a 2% MeOH-YNBw/oa.a. plate to isolate single colonies. One of the resulting single colonies was named GCP101.

(2) Culturing of the Strain (First Seed Culture)

A 1 ml portion of the strain which had been frozen in glycerol was inoculated into a 1,000 ml baffled Erlenmeyer flask containing 200 ml of YPD medium (see Table 1) and cultured at 30° C. for 24 hours with shaking.

TABLE 1

| Composition of YPD medium | |
|---|---|
| Components | Concentration (g/L) |
| Yeast extract | 10 |
| Peptone | 20 |
| Glucose | 20 |

(Second Seed Culture)

The first seed culture broth was inoculated into a 10 liter-jar fermentor containing 5 liters of YPD medium, and the second seed culturing was carried out at 30° C. for 24 hours with agitation. The agitation rate was controlled so that the level of dissolved oxygen in the medium was maintained at approximately 50% of the saturated dissolved oxygen concentration. In the seed culturing, the pH of the medium was not controlled.

(Main Culture)

The second seed culture broth was transferred into a 1,200 liter-fermentor containing 250 liters of a batch culture medium (see Table 2), and batch culturing was started with agitation and aeration. The agitation rate was controlled so that the level of dissolved oxygen in the medium was maintained at approximately 50 to 30% of the saturated dissolved oxygen concentration. When the glycerol in the batch culture medium was consumed, addition of a feeding medium (see Table 3) was started. The medium pH was controlled at a fixed level of 5.85. An antifoam agent was added to the culture medium for defoamation as required.

TABLE 2

| Composition of batch culture medium | |
|---|---|
| Components | Amount per liter |
| Glycerol | 50.0 g |
| $H_3PO_4$ (85%) | 14.0 ml |
| $CaSO_4 \cdot 2H_2O$ | 0.6 g |

TABLE 2-continued

Composition of batch culture medium

| Components | Amount per liter |
|---|---|
| $K_2SO_4$ | 9.5 g |
| $MgSO_4.7H_2O$ | 7.8 g |
| KOH | 2.6 g |
| Biotin solution *1 | 1.6 ml |
| YTM solution *2 | 4.4 ml |
| $FeSO_4.7H_2O$ | 65.0 g |
| $CuSO_4.5H_2O$ | 6.0 g |
| $ZnSO_4.7H_2O$ | 20.0 g |
| $MnSO_4.4-5H_2O$ | 3.0 g |
| $H_2SO_4$ | 5.0 ml |

*1 Biotin solution: 0.2 g/l
*2 YTM solution has the following composition:

TABLE 3

Composition of feeding medium

| Components | Amount |
|---|---|
| YTM solution | 2 ml |
| Methanol | 1,000 ml |

REFERENCE EXAMPLE 2

An HSA expression plasmid pMM042 was constructed using an $AOX_2$ promoter (a mutant of the natural $AOX_2$ promoter (YEAST, 5, 167–177, 1988; Mol. Cell. Biol., 9, 1316–1323, 1989), in which the 255th base upstream from the initiation codon of said promoter is changed from T to C) isolated from the strain GCP101 obtained in Reference Example 1. The thus constructed plasmid was introduced into Pichia pastoris GTS115 to obtain a transformant UHG42-3 (JP-A-4-299984 or EP-A-506040). Thereafter, the thus obtained transformant was cultured in accordance with the above method described in Reference Example 1, thereby allowing the transformant to produce HSA.

REFERENCE EXAMPLE 3

(1) Isolation of Culture Supernatant—Membrane Fractions (I) and (II)

About an 800 liter portion of the culture broth obtained in Reference Example 1 or 2 was subjected to a filter press to isolate the culture supernatant. The resulting supernatant subsequently was passed through an ultrafiltration membrane having a molecular weight exclusion limit of 300,000. Then, the resulting filtrate was concentrated to a volume of about 80 liters using an ultrafiltration membrane having a molecular weight exclusion limit of 30,000 (membrane fraction (I)). Next, the membrane fraction (I) was heat-treated at 60° C. for 3 hours in the presence of 5 mM of sodium caprylate, 10 mM of cysteine and 100 mM of aminoguanidine at pH 7.5. The thus heat-treated solution was cooled down rapidly to about 15° C., adjusted to pH 4.5 and then treated with an ultrafiltration membrane having a molecular weight exclusion limit of 300,000 (membrane fraction (II)). Thereafter, using an ultrafiltration membrane having a molecular weight exclusion limit of 30,000, the buffer in the resulting albumin solution was replaced by a 50 mM acetate buffer (pH 4.5) containing 50 mM of sodium chloride.

(2) Cation Exchanger Treatment

The albumin solution obtained in the above step (1) was applied to a column packed with S-Sepharose that had been equilibrated in advance with a 50 mM acetate buffer (pH 4.5) containing 50 mM of sodium chloride, the column was washed thoroughly with the same buffer and then elution was carried out with a 0.1M phosphate buffer (pH 9) containing 0.3M sodium chloride.

(3) Hydrophobic Chromatography

The HSA solution eluted from the S-Sepharose column was applied to a column packed with Phenyl Cellulofine which had been equilibrated in advance with a 50 mM phosphate buffer (pH 6.8) containing 0.15M sodium chloride. Since HSA does not adsorb to Phenyl Cellulofine under such conditions, the HSA fractions that passed through the column were collected. The HSA solution thus recovered was concentrated to a volume of about 50 liters using an ultrafiltration membrane having a molecular weight exclusion limit of 30,000, and at the same time, the buffer in the HSA solution was replaced by a 50 mM phosphate buffer (pH 6.8).

(4) Anion Exchanger Treatment

The HSA solution thus treated with hydrophobic chromatography, concentrated and buffer-exchanged was applied to a column packed with DEAE-Sepharose which had been equilibrated in advance with a 50 mM phosphate buffer (pH 6.8). Under such conditions, HSA was not adsorbed to the DEAE-Sepharose but passed through the column.

(5) Chelate Resin Treatment

A 1 ml portion of the 25 w/v % solution of purified HSA was mixed with 1 g of DIAION CRB02 (a chelate resin having a styrene-divinylbenzene copolymer as the carrier portion and an N-methylglucamine group as the ligand portion, manufactured by Mitsubishi Kasei Corp.), and the resulting mixture was stirred for 24 hours at room temperature at pH 6.8 and ionic strength of 5 mmho. The resin then was washed with distilled water to recover the non-absorbed HSA-containing fraction.

(6) Borate Treatment

The HSA concentration was adjusted to 2.5 w/v % so that the electric conductivity became 1 mS or below. Calcium tetraborate was added to the resulting solution to a final concentration of 100 mM and a pH value of the solution was adjusted to 9.5. After allowing the solution to stand for 10 hours, the precipitate formed was removed to recover the supernatant, which was then concentrated and desalted. Then, the resulting solution was passed through a ultrafiltration membrane having a molecular weight exclusion limit of about 100,000.

EXAMPLE 1

About an 800 liter portion of the culture broth obtained in Reference Example 1 or 2 was subjected to a filter press to isolate the culture supernatant. The resulting supernatant subsequently was passed through an ultrafiltration membrane having a molecular weight exclusion limit of 300,000. Then, the resulting filtrate was concentrated to a volume of about 80 liters using an ultrafiltration membrane having a molecular weight exclusion limit of 30,000 (membrane fraction (I)).

Next, the resulting concentrate was heat-treated at 60° C. for 3 hours in the presence of 5 mM of sodium caprylate, 5 mM of acetyltryptophane, 100 mM of aminoguanidine and 10 mM of cysteine at pH 7.5. The degree of coloring (a ratio of absorbance at 350 nm to absorbance at 280 nm, hereinafter referred to as $A_{350}/A_{280}$) measured after the treatment with cysteine was decreased by 23%, as compared with that measured before the treatment.

EXAMPLE 2

The fraction obtained in the anion exchanger treatment (4) in Reference Example 3 was used. A reducing agent as listed in Table 4 was added to the fraction so as to give a final concentration of 1%. The HSA concentration was adjusted to 0.5% and the pH was adjusted to 9. Then, the resulting solution was allowed to stand at 37° C. for 24 hours. The results are shown in Table 4.

TABLE 4

| Reducing agent (1%) | Degree of coloring ($A_{350}/A_{280}$) |
|---|---|
| Sodium sulfite | 0.0296 |
| Sodium hyposulfite | 0.0283 |
| Phosphorous acid-sodium sulfite | 0.0269 |
| Phosphorous acid-potassium pyrosulfite | 0.0249 |
| Sulfurous acid-sodium pyrophosphate | 0.0272 |
| Before treatment | 0.0359 |

As shown in Table 4, the degree of coloring was decreased by 20 to 30% in the case of using any reducing agent.

EXAMPLE 3

The fraction obtained in the anion exchanger treatment (4) in Reference Example 3 was used. Ascorbic acid was added to the fraction so as to give a final concentration of 1%. The HSA concentration was adjusted to 0.5% and the pH was adjusted to 4.5. Then, the resulting solution was allowed to stand at 15° C. for 24 hours. The results are shown in Table 5.

TABLE 5

| Reducing agent (1%) | Degree of coloring ($A_{350}/A_{280}$) |
|---|---|
| After treatment | 0.0288 |
| Before treatment | 0.0359 |

As shown in Table 5, the degree of coloring was decreased by 20% in the case of using ascorbic acid.

EXAMPLE 4

Influence of pH

The fraction obtained in the anion exchanger treatment (4) in Reference Example 3 was used. A reducing agent (sodium sulfite) was added to the fraction so as to give a final concentration of 1%. The HSA concentration was adjusted to 0.5% and the pH was adjusted to 7, 8, 9 and 10. Then, the resulting solution was allowed to stand at 37° C. for 12 hours. The results are shown in Table 6.

TABLE 6

| pH | Degree of coloring ($A_{350}/A_{280}$) |
|---|---|
| 7 | 0.0302 |
| 8 | 0.0278 |
| 9 | 0.0272 |
| 10 | 0.0282 |
| Before treatment | 0.0359 |

As shown in Table 6, the degree of coloring was decreased at any pH (pH 7 to 10). Particularly, excellent effects of the reducing treatment can be obtained at pH 8 and pH 9. In this instance, the degree of coloring was decreased by 23 to 24%.

EXAMPLE 5

The fraction obtained in the anion exchanger treatment (4) in Reference Example 3 was used. A reducing agent (sodium sulfite and phosphorous acid-potassium pyrosulfite) was added to the fraction to a concentration of 1, 2 and 3%. The HSA concentration was adjusted to 0.3 and 5% and the pH was adjusted to 9. Then, the resulting solution was allowed to stand at 15° C. for 2 days and 5 days. After the treatment, the solution was dialyzed against 50 mM phosphate buffer (pH 6.5) containing 0.3% of sodium chloride to remove the reducing agent. The results are shown in Table 7.

TABLE 7

| Reducing agent | | Conc. of HSA (%) | Treating period (days) | Degree of coloring ($A_{350}/A_{280}$) |
|---|---|---|---|---|
| Before treatment | | | | 0.0359 |
| No addition | | 0.3 | 5 | 0.0305 |
| Sodium sulfite | 1% | 0.3 | 2 | 0.0243 |
| | 1% | 0.3 | 5 | 0.0230 |
| | 2% | 5 | 2 | 0.0231 |
| | 2% | 5 | 5 | 0.0208 |
| | 3% | 0.3 | 5 | 0.0230 |
| Phosphorous acid-potassium pyrosulfite | 1% | 0.3 | 2 | 0.0230 |
| | 1% | 0.3 | 5 | 0.0215 |
| | 2% | 5 | 2 | 0.0286 |
| | 2% | 5 | 5 | 0.0206 |
| | 3% | 0.3 | 5 | 0.0199 |

As shown in Table 7, the degree of coloring was decreased by 30 to 45% in every test run.

EXAMPLE 6

Effect of Treatment with a Reducing Agent in Each Purification Step

The effect of the treatment with the reducing agent was examined in each purification step. The HSA fractions obtained in the cation exchanger treatment (2), the hydrophobic chromatography treatment (3) and the anion exchanger treatment (4) in Reference Example 3 were adjusted to have an HSA concentration of 0.3%. A reducing agent (phosphorous acid-potassium pyrosulfite) was added to each fraction to a concentration of 2% and the pH was adjusted to 9. Then, the resulting solution was allowed to stand at 15° C. for 5 days. After the treatment, the solution was dialyzed against 50 mM phosphate buffer (pH 6.5) containing 0.3% of sodium chloride to remove the reducing agent. The results are shown in Table 8.

TABLE 8

| HSA fraction | Reducing treatment | Degree of coloring | | | |
|---|---|---|---|---|---|
| | | ($A_{350}/A_{280}$) | ($A_{400}/A_{280}$) | ($A_{450}/A_{280}$) | ($A_{500}/A_{280}$) |
| After cation exchanger treatment | before | 0.0232 | 0.0176 | 0.0106 | 0.0081 |
| | after | 0.0232 | 0.0160 | 0.0076 | 0.0059 |
| After hydrophobic chromatography treatment | before | 0.0300 | 0.0184 | 0.0110 | 0.0075 |
| | after | 0.0242 | 0.0145 | 0.0065 | 0.0042 |
| After anion exchanger treatment | before | 0.0166 | 0.0088 | 0.0051 | 0.0046 |
| | after | 0.0161 | 0.0085 | 0.0049 | 0.0039 |

As shown in Table 8, good decoloring effects can be obtained in each purification step. Particularly, the decoloring effect is remarkable in the long wavelength region.

EXAMPLE 7

Purification Treatment Together with Reducing Agent Treatment

The decoloring effect was examined when the purification step (anion exchanger treatment (4) in Reference Example 3) was carried out in the presence of a reducing agent. Thus, the HSA solution was brought into contact with Q-Sepharose (Pharmacia) using 50 mM tris-hydrochloride buffer (pH 9) containing a reducing agent (sodium sulfite and phosphorous acid-potassium pyrosulfite) and allowed to stand overnight at room temperature. After washing with 50 mM tris-hydrochloride buffer (pH 9) to remove the reducing agent, the HSA was eluted with 50 mM tris-hydrochloride buffer (pH 9) containing 1M sodium chloride. Table 9 shows the degree of coloring of the thus-purified HSA.

TABLE 9

| Reducing agent | | Degree of coloring ($A_{350}/A_{280}$) |
|---|---|---|
| Sodium sulfite | 0.5% | 0.0319 |
| | 0.1% | 0.0324 |
| Phosphorous acid-potassium pyrosulfite | 0.1% | 0.0339 |
| No addition | | 0.0390 |

When the anion exchanger treatment is carried out in the presence of the reducing agent, good decoloring effect can be obtained in the concentration of the reducing agent ranging from 0.1 to 0.5%.

EXAMPLE 8

The HSA solution resulting from the heat treatment of the membrane fraction (I) at 60° C. for 3 hours in Reference Example 3 (1) was dialyzed against a buffer (pH 4) containing 10 mM cysteine at 15° C. and thereafter allowed to stand for 16 hours. As a result, the degree of coloring ($A_{350}/A_{280}$) after the heat treatment was 0.1, while it was decreased to 0.066 after the treatment with the reducing agent.

EXAMPLE 9

About an 800 liter portion of the culture broth obtained in Reference Example 1 or 2 was subjected to a filter press to isolate the culture supernatant. The resulting supernatant subsequently was passed through an ultrafiltration membrane having a molecular weight exclusion limit of 300,000. Then, the resulting filtrate was concentrated to a volume of about 80 liters using an ultrafiltration membrane having a molecular weight exclusion limit of 30,000 (membrane fraction (I)).

The resulting concentrate was adjusted to pH 4.5 and then treated with an ultrafiltration membrane having a molecular weight exclusion limit of 300,000 (membrane fraction (II)). Thereafter, using an ultrafiltration membrane having a molecular weight exclusion limit of 30,000, the buffer in the resulting albumin solution was replaced by a 50 mM acetate buffer (pH 4.5) containing 50 mM of sodium chloride. The albumin solution thus obtained was applied to a column packed with S-Sepharose that had been equilibrated in advance with a 50 mM acetate buffer (pH 4.5) containing 50 mM of sodium chloride, the column was washed thoroughly with the same buffer and then elution was carried out with a 0.1M phosphate buffer (pH 9) containing 0.3M sodium chloride. Before and after the treatment with S-Sepharose, the HSA fraction was examined for the free polysaccharide content by means of the phenol-sulfuric acid method. As a result, the free polysaccharide content was decreased to 1/20 after the treatment. The HSA solution eluted from the S-Sepharose column was heat-treated at 60° C. for 1 hour in the presence of 5 mM of sodium caprylate, 5 mM of acetyltryptophane, 100 mM of aminoguanidine and 10 mM of cysteine at pH 7.5. The $A_{150}/A_{280}$ value measured after the treatment with cysteine was 50% decreased as compared with that measured before the treatment.

EXAMPLE 10

Relation Between Decoloring Effect and the Order of Cation Exchanger Treatment and Heat Treatment About an 800 liter portion of the culture broth obtained in Reference Example 1 or 2 was subjected to a filter press to isolate the culture supernatant. The resulting supernatant subsequently was passed through an ultrafiltration membrane having a molecular weight exclusion limit of 300,000. Then, the resulting filtrate was concentrated to a volume of about 80 liters using an ultrafiltration membrane having a molecular weight exclusion limit of 30,000 (membrane fraction (I)). The resulting concentrate was adjusted to pH 4.5 and then treated with an ultrafiltration membrane having a molecular weight exclusion limit of 300,000 (membrane fraction (II)). The thus-obtained fraction was subjected to the following experiments.

(1) The fraction was treated with the cation exchanger in the same manner as in Example 9 followed by heat treatment. The free polysaccharide content in the membrane fraction (II) was approximately 110 mg/ml and that in the eluate resulted from the cation exchanger treatment was 5 mg/ml when the HSA concentration was 250 mg/ml.

(2) The procedure of Example 9 was repeated except that the heat treatment was followed by the cation exchanger treatment.

In each experiment, the degree of coloring of the HSA fraction obtained in each step was measured and compared. The results are shown in Table 10.

TABLE 10

| Treatment | Degree of coloring ($A_{350}/A_{280}$) |
|---|---|
| Cation exchanger treatment | 0.0688 |
| Cation exchanger treatment followed by heat treatment | 0.0309 |
| Heat treatment | 0.0674 |
| Heat treatment followed by cation exchanger treatment | 0.0428 |
| Membrane fraction (II) | 0.0700 |

As shown in Table 10, when the cation exchanger treatment was followed by the heat treatment, the degree of coloring before the treatment was decreased 55% after the heat treatment. In contrast, when the heat treatment was followed by the cation exchanger treatment, the degree of coloring was decreased 36%. Thus, the former procedure can suppress the degree of coloring as compared with the latter procedure. It is considered that this difference is attributed to removal of a considerable amount of free polysaccharides in the HSA fraction by the cation exchanger treatment.

EXAMPLE 11

Relation Between Decoloring Effect and Timing of Heat Treatment During the Purification Procedure Based on the purification procedure of HSA according to Reference Example 3, relation between the timing of the heat treatment and the decoloring effect was examined. In Reference Example 3, the heat treatment was carried out immediately before the cation exchanger treatment. The degree of coloring was compared in the case that the heat treatment was carried out as the final step, in the case that the heat treatment was carried out immediately after the cation exchanger treatment and in the case that the heat treatment was additionally carried out at the final step. The heat treatment conditions in Example 9 were followed. The results are shown in Table 11.

TABLE 11

| Timing of heat treatment | Treating Procedure* | Degree of coloring ($A_{350}/A_{280}$) |
|---|---|---|
| Filter press (starting step) | (1) | 0.078 |
| No heat treatment | (1)-(2)-(3)-(4)-(5)-(6) | 0.025 |
| Immediately before cation exchanger treatment | (1)-o-(2)-(3)-(4)-(5)-(6) | 0.019 |
| Final step | (1)-(2)-(3)-(4)-(5)-(6)-o | 0.016 |
| Immediately before cation exchanger treatment and at final step | (1)o-(2)-(3)-(4)-(5)-(6)-o | 0.015 |
| Immediately after cation exchanger treatment | (1)-(2)-o-(3)-(4)-(5)-(6) | 0.016 |

Note:
*in the treatment procedure, (1) to (6) and o stand for the following treatment
(1) filter press
(2) cation exchanger treatment
(3) hydrophobic chromatography
(4) anion exchanger treatment
(5) chelate resin treatment
(6) calcium borate treatment
o heat treatment While the invention has been described in detail and with reference to specific embodiments thereof, it will be apparent to one skilled in the art that various changes and changes and modifications can be made therein without departing from the spirit and scope thereof.

What is claimed is:

1. A method for decoloring a recombinant human serum albumin, which comprises treating a recombinant human serum albumin (HSA), during purification thereof except in a heat treatment, with a reducing agent, thereby decoloring the recombinant HSA.

2. The method according to claim 1, wherein the reducing agent is a low molecular weight compound containing an SH group selected from the group consisting of cysteine, cysteamine, cystamine, aminopropanethiol, methionine, ethionine and glutathione, or is sulfurous acid, hyposulfurous acid, pyrosulfurour acid, phosphorous acid-sulfurous acid, phosphorous acid-pyrosulfurous acid, sulfurous acid-pyrophosphoric acid, ascorbic acid, or a salt thereof.

3. The method according to claim 1, wherein the recombinant human serum albumin concentration is from 0.01 to 25 w/v % during the treatment with the reducing agent.

4. The method according to claim 1, wherein the recombinant human serum albumin concentration is from 0.1 to 5 w/v % during the treatment with the reducing agent.

5. The method according to claim 1, wherein an amine compound known to suppress coloration of human serum albumin is present during the treatment with the reducing agent.

6. A method for decoloring a recombinant human serum albumin (HSA), which comprises removing free polysaccharides from a recombinant human serum albumin and then heat treating said albumin in the presence of a reducing agent, thereby decoloring the recombinant HSA.

7. The method according to claim 6 wherein the treatment with the reducing agent is carried out at from 10° to 100° C. for 10 minutes to 240 hours.

8. The method according to claim 6, wherein the treatment with the reducing agent is carried out at from 20° to 80° C. for 30 minutes to 120 hours.

9. The method according to claim 2, wherein the recombinant human serum albumin to be heat treated has a free polysaccharide content of not more than 5 mg/ml when the HSA concentration is 250 mg/ml.

10. The method according to claim 6, wherein the heat treatment is carried out in the presence of a stabilizer.

11. The method according to claim 6, wherein an amine compound known to suppress coloration of human serum albumin is present during the heat treatment.

12. A method for decoloring a recombinant human serum albumin, which comprises treating a recombinant human serum albumin (HSA) with a cation exchanger to remove free polysaccharides therefrom and then heat treating said albumin in the presence of a reducing agent, thereby decoloring the recombinant HSA.

13. The method according to claim 12, wherein the recombinant human serum albumin to be heat treated has a free polysaccharide content of not more than 5 mg/ml when the HSA concentration is 250 mg/ml.

14. The method according to claim 12, wherein the heat treatment is carried out in the presence of a stabilizer.

15. The method according to claim 12, wherein an amine compound known to suppress coloration of human serum albumin is present during the heat treatment.

* * * * *